United States Patent
Weiss et al.

(10) Patent No.: US 6,527,731 B2
(45) Date of Patent: Mar. 4, 2003

(54) CONTROL SYSTEMS FOR BIOPSY DEVICES

(76) Inventors: David Weiss, House No. 57, Moshav Hemed 50295 (IL); Mordechai Weiss, 52 Zahal Street, Yahud 56265 (IL)

(*) Notice: Subject to any disclaimer, the term of this patent is extended or adjusted under 35 U.S.C. 154(b) by 0 days.

(21) Appl. No.: 09/850,535

(22) Filed: May 7, 2001

(65) Prior Publication Data

US 2002/0082518 A1 Jun. 27, 2002

(30) Foreign Application Priority Data

Dec. 22, 2000 (IL) ................................................ 140494

(51) Int. Cl.$^7$ ............................................. A61B 10/00

(52) U.S. Cl. ....................................... 600/566; 600/568

(58) Field of Search ................................ 600/567, 568, 600/566; 606/170

(56) References Cited

U.S. PATENT DOCUMENTS

| | | | |
|---|---|---|---|
| 4,763,662 A | | 8/1988 | Yokoi |
| 5,415,169 A | | 5/1995 | Siczek et al. |
| 5,493,130 A | | 2/1996 | Dennison et al. |
| 5,494,039 A | | 2/1996 | Onik et al. |
| 5,549,112 A | | 8/1996 | Cockburn et al. |
| 5,647,373 A | | 7/1997 | Paltieli |
| 5,769,086 A | * | 6/1998 | Ritchart et al. ............. 600/566 |
| 5,924,992 A | | 7/1999 | Park et al. |
| 5,947,964 A | * | 9/1999 | Eggers et al. .................. 606/41 |
| 5,980,469 A | | 11/1999 | Burbank et al. |
| 6,017,316 A | | 1/2000 | Ritchart et al. |
| 6,027,457 A | | 2/2000 | Shmulewitz et al. |
| 6,155,988 A | * | 12/2000 | Peters ......................... 600/564 |
| 6,193,673 B1 | * | 2/2001 | Viola et al. .................. 600/568 |
| 6,273,862 B1 | * | 8/2001 | Privitera et al. ............. 600/568 |
| 6,344,026 B1 | * | 2/2002 | Burbank et al. ............. 600/567 |

OTHER PUBLICATIONS

Blessed et al., "Obstetrician–gynecologists Performing Genetic Amniocentensis May be Misleading Themselves and Their Patients", Am. J. Obstet Gynecol 184:1340–1344, 2001.

Boerner et al., "Ultrasound–Guided Fine–Needle Aspiration (FNA) of Nonpalpable Breast Lesions", Cancer 87:19–23, 199.

Cheung et al, "Sonographically Guided Core–Needle Biopsy in the Diagnosis of Superficial Lymphadenopathy", Journal of Clinical Ultrasound 28:283–289, 2000.

Feld et al., "Dramatic Increase in Ultrasound–Guided Interventional Procedure Volume", 217:485, No. 1164, 2000.

(List continued on next page.)

*Primary Examiner*—Henry Bennett
*Assistant Examiner*—Vinod D Patel
(74) *Attorney, Agent, or Firm*—Fish & Richardson P.C.

(57) ABSTRACT

A system adapted to control the operation of a fine needle aspiration (FNA) biopsy device provided with a syringe to which is transferred a tissue sample extracted from an internal target in the body of a patient in which the needle is injected. Associated with, this biopsy device is an ultrasound imaging instrument having a transducer placed on a body site overlying the internal target and coupled to a CRT monitor. The needle is injected into the patient through a guide passage in the transducer, hence displayed on the CRT screen is an image of the internal target and that of the advancing needle. The biopsy device is controlled by a pneumatic or motor-driven mechanism operatively coupled to a guide tube through which the needle extends. For a first phase of an operating cycle, the mechanism advances the needle toward the target to extract a tissue sample therefrom. In a second operating phase, the mechanism acts to retract the tissue loaded needle from the body of the patient. And in the final phase of the operating cycle, the sample is transferred from the needle to the syringe from which it can be removed for analyses.

16 Claims, 4 Drawing Sheets

OTHER PUBLICATIONS

Hatada et al., "Ultrasound–Guided Fine–needle Aspiration Biopsy for Breast Tumors: Needle Guide Versus Freehand Technique", Tumori 85:12–4, 1999.

Hsu et al., "Ultrasound–Guided Fine–Needle Aspiration Biopsy of Lung Cancers", J. Clin Ultrasound 24:225–233, 1996.

Newkirk et al., "Ultrasound–Guided Fine–needle Aspiration and Thyroid Disease", Otolaryngology–Head and Neck Surgery 123:700–705, 2000.

Rubin et al., "Reducing the Cost of Diagnosis of Breast Carcinoma", Cancer 91:324–332, 2001.

Saifuddin et al., "Ultrasound–Gided Needle Biopsy of Primary Bone Tumours" The JOurnal of Bone and Joint Surgery 82:50–54, 2000.

Zanetta et al., "Transvaginal Ultrasound–Guided Fine Needle Sampling of Deep Cancer Recurrences in the Pelvis: Usefulness and Limitations", Gynecologic Oncology 54:59–63. 1994.

* cited by examiner

CONTROL SYSTEMS FOR BIOPSY DEVICES

FIELD OF THE INVENTION

This invention relates generally to fine needle aspiration (FNA), biopsy devices, and in particular to control systems for automatically controlling the operation of an FNA biopsy device so as to carry out a biopsy procedure.

STATUS OF PRIOR ART

A biopsy procedure involves the extraction of a small sample of living tissue from an internal mass in a patient, the extracted sample being then examined under a microscope in order to diagnose the patient's condition. Where and how a biopsy is to be performed depends on the internal site of the suspected mass. A biopsy is usually called for when other diagnostic techniques are unable to supply sufficient information on which to base a diagnosis. Thus a physician can by means of an ultrasound imaging instrument locate and observe an internal tumor in the body of a patient. But an ultrasound image of this tumor does not indicate whether it is benign or malignant. A biopsy is therefore necessary to make this determination.

A biopsy can be conducted either by an open or by a percutaneous method. An open biopsy entails an invasive surgical procedure to expose the internal region of interest so that one can then excise a portion of the suspected mass and examine it under a microscope. In a percutaneous biopsy, a large bore needle is used, making it necessary to make an incision in order to obtain a tissue sample from a suspected mass. A large bore needle carries with it the risk of tumor seeding along the biopsy tract.

The present invention deals with the least disturbing of biopsy techniques; namely: "Fine Needle Aspiration" (FNA). In an FNA technique, a fine needle projecting from a syringe is injected into a patient to impinge on an internal target from which the needle extracts a tissue sample constituted by a cluster of cells. The small sample picked up by the needle is then sucked into the syringe for cytologic examination under a microscope.

In an FNA biopsy procedure, it is vital that the injected needle be accurately directed to strike the target of interest and avoid adjacent tissues. When the target is palpable, such as a bulging thyroid gland, a physician has no difficulty in directing the needle toward the target. In this situation, all that a physician need do is to grasp in one hand the bulging tissue mass and with his other hand to inject the needle of the FNA device into the mass to extract a sample therefrom. The syringe is then operated to suck the sample from the needle into the syringe from which the sample is later removed for examination To facilitate such manual operations, various devices have been devised to hold the biopsy syringe. One such device for this purpose is disclosed in U.S. Pat. No. 5,493,130.

In those situations where the target for an FNA biopsy is not palpable but is deeply embedded in a patient's body, such as in the liver, then in order to be able to guide the needle toward the internal target one must be assisted by an imaging instrument, making it possible for the physician to see the internal target and the position of the fine needle relative thereto. The imaging instrument used for this purpose may be an ultrasound instrument or a computer-assisted tomograph (CAT or CT).

In the medical field, the reason ultrasound imaging is a preferred diagnostic tool is because of the non-ionizing character of ultrasound radiation. This makes ultrasound imaging safe and innocuous so that a patient may be repeatedly subjected in an ultrasound examination.

Sounds generated in an ultrasound instrument lie within a 1 to 10 mHz frequency range. These sounds are produced by a piezoelectric transducer caused to vibrate by an electronic pulse generator. When placed at a site overlying an internal target of interest, the piezoelectric transducer emits sonic pulses which are propagated through the body of the patient and reflected by interfaces between tissues having different acoustic impedances, thereby producing echo pulses which are received by the transducer. Signals from the transducer are applied to the cathode ray tube (CRT) of a monitor associated with the transducer on whose screen is displayed an image of the internal target of interest and the tissue to surrounding the target.

In order for an ultrasound instrument to accurately lead the needle of an FNA biopsy device toward an internal target when tissues are suspect and require diagnosis, it is known to provide the transducer of the instrument with a needle guide, such as the needle guide disclosed in the U.S. Pat. No. 5,924,992 to Park et al. This needle guide makes it possible for a physician to see on the CRT screen of the monitor associated with the transducer an image of the target of interest and of the biopsy needle as it advances toward this target. Also of prior art interest in regard to the use of an ultrasound instrument to perform real-time image-guided biopsy of tissue is U.S. Pat, 6,027,457 to Shmulewitz et al.

A biopsy needle guide for use with an ultrasonic probe in a medical procedure to accurately position a biopsy needle with respect to an internal target is also disclosed in U.S. Pat. 5,494,039 to Onik et al.

A needle inserting guide associated with an ultrasound probe makes it possible for a physician to properly direct the needle toward an internal target. But the guide does not relieve the physician of the need to manually operate the biopsy device so as to advance the needle toward the target to extract therefrom a tissue sample, to then withdraw the sample from the target, and finally to transfer the sample from the needle to the syringe.

Moreover, while the needle insertion guide simplifies the spatial relationship of the needle, the ultrasound probe and the internal target being biopsied it is an impediment to navigation and to a clear three-dimensional display of the tissues. One can therefore understand why investigators have reported that the sensitivity of a free-hand biopsy is greater than the sensitivity of a needle guide technique (see—Hatadet et al. Tumor 1999; 85;12).

Existing biopsy procedures present difficulties to a physician, for he must while viewing the CRT screen of an ultrasound imaging instrument at the same time be holding the transducer of this instrument against the body of the patient, and as he holds this transducer with one hand, he must with his other hand manipulate the FNA device first to inject the needle into the patient to obtain a sample, second to withdraw the needle, and third to operate the syringe to transfer the sample thereto.

A logical form of automatic control system for an FNA biopsy device would be a system in which electrically-powered miniature motors act to advance and retract the fine needle to extract a tissue sample from an internal target, and to then manipulate the syringe to transfer the sample from the needle to the syringe.

Of prior art interest in regard to a motor-driven automated biopsy device is the U.S. Pat. 5,980,469 to Burbank et al. However, conventional electrically-powered motors in a control system associated with a biopsy device in proximity to an ultrasound transducer through which the needle is guided cannot be tolerated. The reason for this is that relatively strong magnetic fields emanating from the motors and enveloping the transducer may interfere with its operation and distort the images appearing in the CRT screen. Moreover, a conventional motorized control system for a biopsy device which must be held by a physician in the course of a biopsy procedure enlarges the bulk and weight of the device and therefore makes it more difficult to handle.

Another drawback of a motor driven biopsy device is that it is difficult with a conventional motor to advance or retract the needle to the precise degree required by a biopsy procedure.

In our pending Israel Patent 140,494 filed Dec. 22, 2000, there is disclosed a pneumatic control system for automatically controlling the operation of an FNA biopsy device to be injected into a patient to extract a tissue sample from an internal target to be transferred to the syringe.

The control system includes a cylinder having a piston slideable therein to which the FNA device is coupled, movement of the piston advancing or retracting the needle. In an operating cycle, a computer-controlled pneumatic supply feeds air at positive pressure into the cylinder in a region above the piston to cause the piston to advance the needle toward the target to extract a tissue sample therefrom, and to then feed air at positive pressure into the cylinder in a region below the piston to cause the needle to retract and withdraw the sample. For the final phase of the operating cycle, air at negative pressure is fed into the syringe, causing the sample to be sucked from the needle into the syringe.

The pneumatic control system disclosed in our pending application acts by means of positive and negative air pressures to fully automate the operation of an FNA biopsy device. But it does not create electromagnetic fields that may disrupt the operation of the ultrasound transducer with which the biopsy device is associated. Of prior art interest in his regard is the automatic control system for a vacuum-assisted core biopsy device disclosed in U.S. Pat. 6,017,316 to Ritchart et al. In the system shown in this patent it is only negative pressures creating a vacuum that is used throughout the control system.

In a biopsy procedure the degree of accuracy required depends on the nature of the target from which a tissue sample is to be extracted. In many situations, all that is necessary is a reasonable degree of accuracy rather than a high degree of precision. However, in some situations, greater precision is desirable.

Thus in a lung biopsy, the needle must make contact with the surface layer of the lung to extract a tissue sample therefrom. But the operator must exercise care to avoid penetrating the lung and causing it to collapse. Yet because it is difficult to precisely position the needle, in a fair percentage of lung biopsy procedures, lung collapse is experienced.

SUMMARY OF THE INVENTION

In view of the foregoing, tile main object of this invention is to provide control systems for automatically controlling the operation of an FNA biopsy device by a pneumatically operated or a motor driven mechanism.

A significant feature of an automatic control system in accordance with the invention is that it relieves a physician conducting an FNA biopsy of the need to manually inject the needle into the patient in order to extract a tissue sample from an internal target and then operate the syringe to transfer the sample thereto from the needle.

More particularly, an object of this invention is to provide an automatically-controlled FNA biopsy device associated with an ultrasound imaging instrument whose transducer has a passage extending therethrough to guide the needle of the device into the body of a patient.

This passage in the transducer or ultrasound probe is through the dead center thereof, as a consequence of which the sensitivity of a free-hand biopsy device is enhanced.

Yet another object of the invention is to provide a control system in which the needle of the FNA biopsy device is advanced by a stepping motor energized by DC pulses whose repetition rate determines the rate at which the needle is advanced toward a final position.

Also an object of this invention is to provide a control system for an FNA biopsy device whose operation is governed by a computer programmed to accommodate the biopsy procedure to the requirements of the patient being treated.

Briefly stated, the objects are attained in a control system for governing the operation of an FNA biopsy device, provided with a syringe and a fine needle projecting therefrom to be injected into a patient to extract from an internal target a tissue sample which is then transferred to the syringe. Associated with the FNA device is an ultrasound imaging instrument having a transducer placed on a body site overlying the internal target and coupled to a CRT monitor. The needle is injected into the patient through a guide passage in the transducer. Hence displayed on the CRT screen is an image of the internal target and that of the advancing needle.

The FNA biopsy device is controlled by a pneumatically-operated or motor-driven mechanism linked to the guide tube through which the needle extends. In a first phase of an operating cycle, the mechanism causes the needle to advance toward the target to extract a tissue sample therefrom. In a second phase, the mechanism acts to retract the needle and withdraw the sample. And in a final phase, the syringe is manipulated to transfer the tissue sample from the needle to the syringe.

BRIEF DESCRIPTION OF THE DRAWINGS

For a better understanding of the invention as well as other objects and features thereof, reference is made to the annexed drawings wherein.

DETAILED DESCRIPTION OF THE INVENTION

The FNA Biopsy Assembly (First Embodiment)

Figure 1:
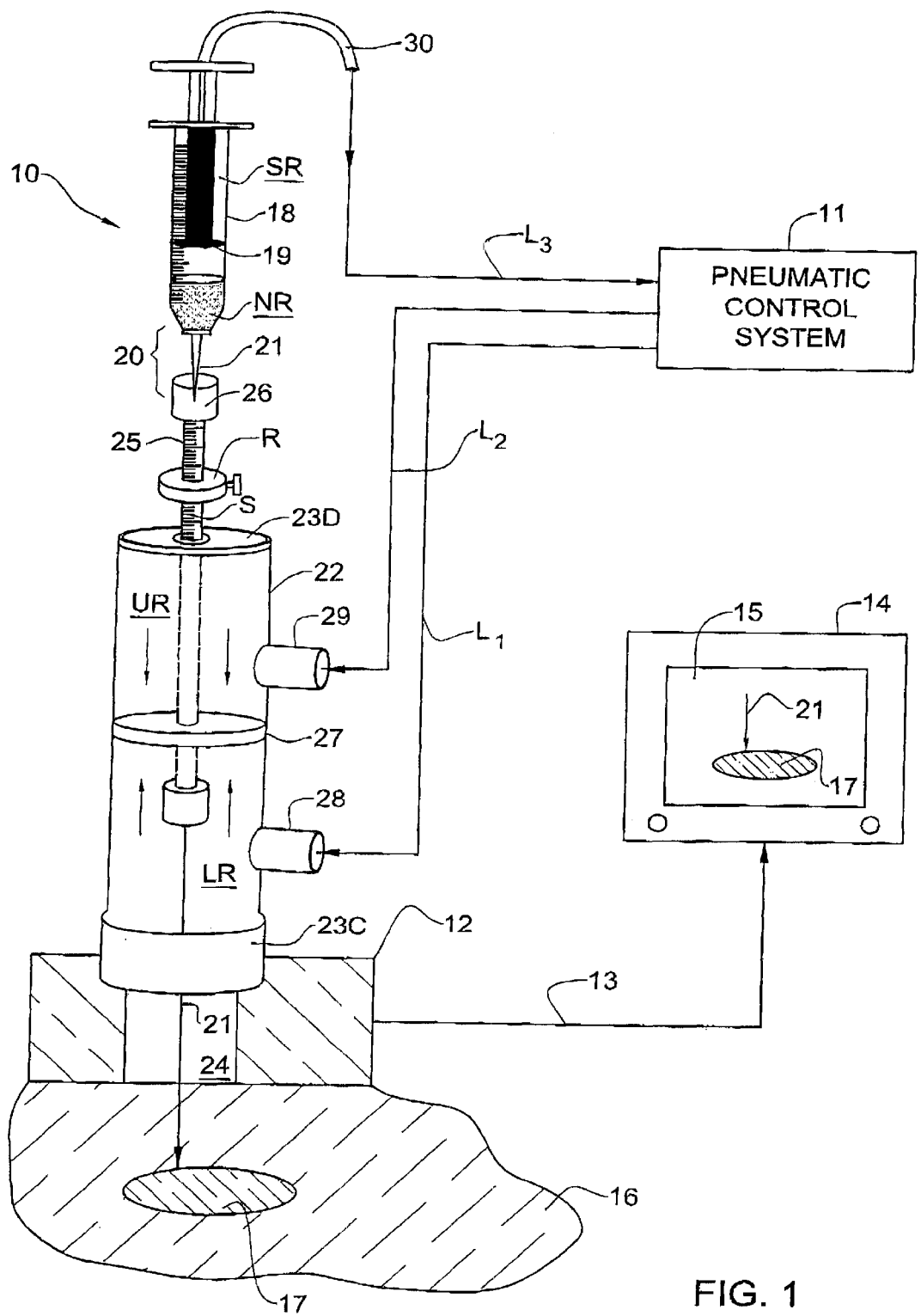
FIG. 1 shows schematically an FNA biopsy device associated with an ultrasound imaging instrument and controlled automatically by a pneumatic control system in accordance with one embodiment of the invention.
Figure 2:
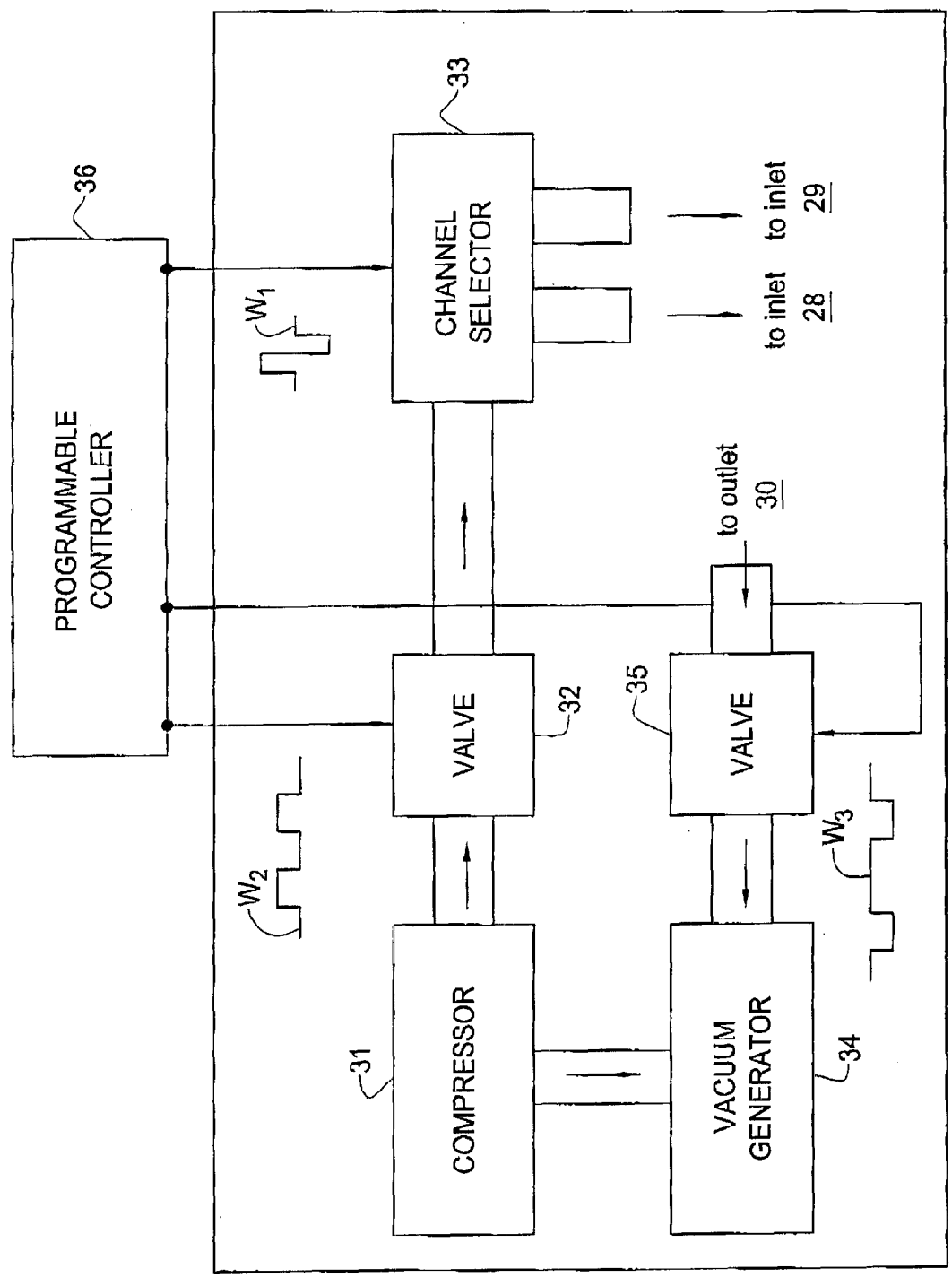
FIG. 2 is a block diagram of the pneumatic control system.

Referring now to FIG. 1, shown therein is an FNA biopsy device, generally identified by numeral 10, the device being controlled by a pneumatic control system 11 whose details are shown in FIG. 2. Associated with biopsy device 10 is an ultrasound imaging instrument that includes a transducer 12, preferably of the piezoelectric type. The biopsy device, together with the ultrasound imaging instrument and the pneumatic control system, form an FNA biopsy assembly in accordance with a preferred embodiment of the invention.

Transducer 12 is coupled by a cable 13 to a monitor 14 provided with a cathode ray tube (CRT) screen 15 whose position is such that images appearing on the screen can be viewed by a physician or by an operator while conducting a biopsy procedure.

Displayed on screen 15 is an image of an internal region of the body 16 of a patient in which is located the suspected mass to be biopsied. By way of example, we shall assume that this mass is a tumor 17 from which a tissue sample is to be extracted by means of biopsy device 10 so that it can be determined whether this tumor is benign or malignant. Transducer 12 is placed by the physician conducting the biopsy at a body site overlying the tumor 17; hence what is seen on CRT screen 15 is an image of tumor 17 and of the surrounding tissues.

FNA biopsy device 10 includes a syringe 18 having a cylindrical vessel in which is slideable a plunger 19 so that when the plunger is pulled toward the upper end of the vessel, it creates a negative pressure to suck tissue in to the vessel. The vessel of syringe 18 has at its lower end a conical nose 20. Projecting from nose 20 in line with the longitudinal axis of the syringe is a fine hollow needle 21 whose length is appropriate to the biopsy to be conducted. Obviously if tumor 17 is deeply embedded in body 16, a longer needle will be required than if the tumor were closer to the surface.

The pneumatic control system 11 for biopsy device 10 includes a cylinder 22 having at its upper end a barrier disc 23D and its lower end a collar 23C, that is seated in a well at the upper face of transducer 12 to anchor the cylinder on the transducer at a position in registration with a central guide passage 24 therein. In practice, the piezoelectric transducer may be in an annular form to create this central guide passage.

Coaxially disposed within cylinder 22 is a guide tube 25 on whose upper end is a socket 26 in which is received nose 20 of the syringe, the elongated needle 21 extending from the nose of the syringe through guide tube 25 into the central guide passage 24 in transducer 12.

Inscribed or otherwise marked along guide tube 25 is a linear scale S which is graduated in terms of depth. Slideable along guide tube 25 on the scale is a stroke-adjusting ring R having a set screw to fix the position of the ring along the scale with respect to barrier disc 23D on the upper end of the cylinder. Hence the position of the ring on the guide tube determines the extent to which the guide tube is permitted to advance when piston 27 is caused to move downwardly in cylinder 22.

Mounted on guide tube 25 at an intermediate position thereon is a disc-shaped piston 27 which is slideable within cylinder 22. When piston 27 is pneumatically driven downwardly in cylinder 22, it then advances needle 21 in the direction of tumor 17, and when piston 27 is pneumatically driven upwardly in cylinder 22, it then retracts the needle from tumor 17.

Cylinder 22 is provided at a lateral position below its midpoint with a lower air inlet 28, and at a lateral position above the midpoint with an upper air inlet 29. Syringe 18 is provided with an air outlet 30 which communicates with the interior of the vessel above plunger 19 therein.

The lower region LR below piston 27 in cylinder 22 is coupled via inlet 28 and line L1 to pneumatic control system 11 which supplies air at positive pressure to this region, causing piston 27 to move upwardly in the cylinder and in doing so, to retract needle 21.

The upper region UR above piston 27 in cylinder 22 is coupled via inlet 29 and line L2 to pneumatic control system 11 which supplies air at positive pressure to this region, causing piston 27 to move downwardly in cylinder 22 and in doing so to advance needle 21 into the body 16 of a patient toward the internal target to be sampled.

The region SR in the vessel of syringe 10 above plunger 19 is coupled via air outlet 30 and line L3 to control system 11 which draws air at negative pressure from region SR to create a vacuum therein driving plunger 19 upwardly in the vessel, and in doing so creating a negative pressure in the region NR in the vessel below the plunger to suck into this region the tissue sample contained in needle 21.

The operating stroke of guide tube 25 when the needle is advanced in the direction of the target is limited by the position of the stroke-adjusting ring R thereon for when this ring engages the barrier disc 23D at the upper end of the cylinder, the advance of the guide tube and of the needle passing through the tube is arrested.

In the biopsy procedure the operator observes on screen 15 the lesion 17 or other target to be biopsied. He then fixes the position of the sliding ring R along the scale S or guide tube 25 at a position that allows needle 21 to reach the lesion and take a sample therefrom.

The Pneumatic Control System

The pneumatic control system 11 included in the assembly, as shown in FIG. 2, is provided with a compressor 31 which supplies air at positive pressure through a valve 32 to a channel selector 33. Selector 33 acts to feed the compressed air either into air inlet 28 in cylinder 22, or into air inlet 29.

Compressor 31 is associated with a vacuum generator 34, air being drawn into compressor 31 from the vacuum generator to produce air at a negative pressure. Vacuum generator 34 is coupled via a valve 35 to the air outlet 30 in syringe 18.

In operation, the physician or other operator after setting the position of a stroke-adjusting ring R that allows the needle to reach the lesion 17 visible on the screen 15, switches channel selector 33 to a first position to supply compressed air through inlet 29 into the upper region UR of cylinder 22. When valve 32 is then turned on, piston 27 is caused to advance the fine needle toward the lesion.

The degree to which valve 32 is opened controls the rate at which needle 21 is advanced toward the tumor. The valve is shut to arrest Her advance of the needle when it has impinged on the tumor or target and taken a tissue sample therefrom.

In order now to retract the needle containing the sample from the tumor, channel selection 33 is switched to a second position to feed compressed air to the lower region LR of the cylinder. Valve 32 is then opened to admit this air to cause piston 37 to move upwardly in the cylinder and in doing so to retract the needle and withdraw the sample from the tumor.

In the final phase of this procedure, valve 35 coupled to vacuum generator 34 is opened to produce a negative air pressure acting to draw air from syringe 18 which pulls plunger 19 upwardly. This creates a negative pressure in the syringe below plunger 19 in the region NR, thereby sucking the tissue sample out of the needle into this region. Hence to examine the sample, it must be taken out of the syringe.

The pneumatic control system 11 shown in FIG. 2 is easy to operate, for all the operator has to do after he sees on the CRT screen an image of the tumor, is to switch the channel selector to a position permitting the biopsy needle to advance and then turn open valve 32 to cause the needle to advance until it is arrested by the stroke limiting ring R when the needle reaches the tumor to take a sample, after which valve 32 is closed. Then to retract the needle now carrying the sample from the tumor, the operator switches channel selector 33 to a position permitting this retraction and he reopens valve 32 to cause the needle to retract. Finally, to cause the sample to be transferred from the needle to the syringe, the operator opens valve 35.

There are advantages to be gained by automating the operation of the assembly by means of a programmable computer 36, for then the biopsy procedure can be programmed to accommodate the requirements of different patients.

Computer 36 is adapted to effect control of channel selector 33, and valves 32 and 35, and for this purpose it is necessary that these elements have electromagnetic actuators so that by the application of a dc control signal, the element is rendered operative.

Thus the program of tie computer is such that in order to operate channel selector 33, it yields a signal having a waveform W1 consisting of a positive pulse for causing the selector to feed compressed air into inlet 28, followed by a negative pulse to cause the selector to feed the compressed air into inlet 29.

The waveform W2 of the signal for operating valve 22 consists of positive rectangular pulses whose duration determines the time during which the valve is open, the intervals between these pulses giving the time during which the valve is shut. Waveform W3 of the signal for operating valve 35 consists of negative pulses whose duration represents the time during which the valve is open to draw air at negative pressure, the intervals between these pulses representing the "off" time of this valve.

Second Embodiment

Figure 3:
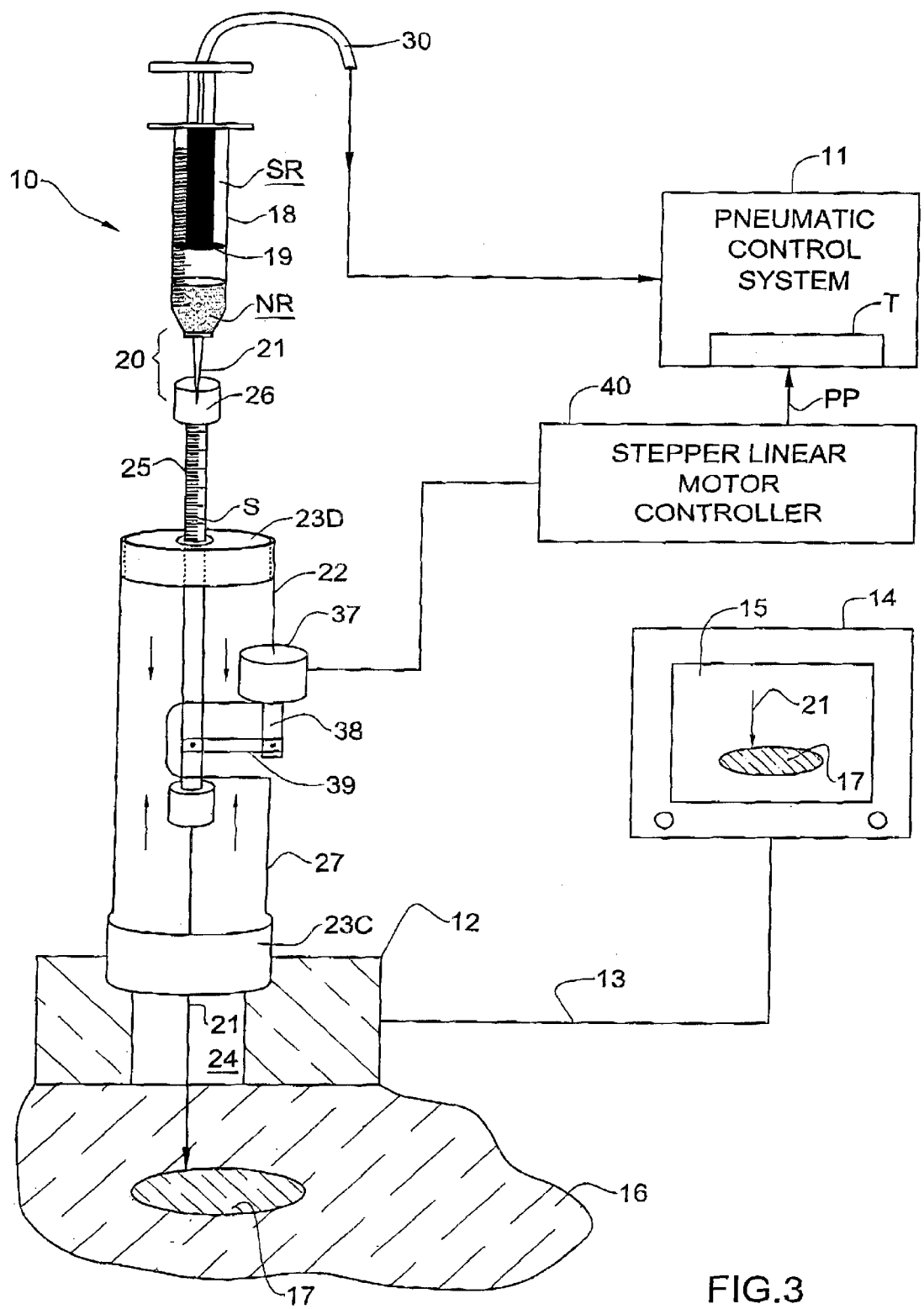
FIG. 3 shows schematically a second embodiment of the invention in which an FNA biopsy device is motor-controlled in the first and second phases of the operating cycle, and pneumatically controlled in the final phase.

In this embodiment which is illustrated in FIG. 3, the control system for the FNA biopsy device is a hybrid of a pneumatically-operated and a motor-driven mechanism. In the fist and second phases of the biopsy procedure in which the needle is advanced to extract a tissue sample from the internal target and then withdrawn, the biopsy device is then driven by a stepping motor. But in the final phase in which the sample contained in them needle is transferred to the syringe, the syringe is then pneumatically driven.

In this hybrid system, mounted on cylinder 27 which is concentric with guide tube 25 in which needle 21 is supported to extend through and beyond the tube is a linear stepping motor 37. Motor 37 is provided with a rack bar 38 which is advanced linearly or retracted in a stepwise manner in a direction which depends on the polarity of the dc pulses which energize the motor.

Rack bar 28 is operatively coupled by a link 39 to guide tube 25, thereby causing the needle 21 extending through the guide tube to advance or retract with respect to internal target 17 in accordance with the linear movement of the rack bar.

The dc pulses applied to stepping motor 37 cause it to rotate a discrete angular step per pulse. A typical step angle can be as small as 0.72 degrees, and as great as 5 degrees and higher. To convert this angular stepping motion to linear motion for translating guide tube 25 through which the hollow FDA needle extends, a pinion (not shown) mounted on the rotor shaft of the motor engages rack bar 28. In this way each angular step taken by the motor is translated into a linear step in a direction that depends on the polarity of the pulses applied to the dc stepping motor.

The advantage gained by using a stepping motor for controlling the movement of the biopsy needle in the first and second phases of the biopsy procedure rather than a pneumatically-driven arrangement is that the stepping action makes possible the accurate positioning of the needle in a repeatable, uniform manner. The degree of precision depends on the predetermined step angle. Obviously if the step angle is one degree so that 360 steps are taken in a full revolution of the motor, one can advance the needle to a more precise position than if the step angle were three degrees.

The dc pulses for energizing the stepping motor are produced by a battery-operated pulse generating unit 40 which is adjustable to provide periodic pulses of a width and magnitude creating the power required to operate the stepping motor. Unit 40 includes a polarity-reversing switch 41 which determines the polarity of the pulses applied to the motor and consequently the direction of translation. In practice the dc power may be obtained from a rectified ac source.

Unit 40 is also provided with a control knob 42 whose pointer traverses a scale calibrated in increments of distance within the -operating range of the biopsy device, such as zero to 5 inches. The setting of this knob determines the distance travelled by the needle in the first phase of the procedure. If therefore knob 42 is set to 3.25 inches, then when the unit is switched on, it will supply to the stepping motor with the exact number of pulses required to bring about the desired needle advance. In this way the needle can be made to penetrate the internal target in the body of a patient to a desired depth—no more or less.

As previously noted, one must avoid the radiation of magnetic fields in the vicinity of the ultrasound transducer applied to the body of the patient, for this field may interfere with the proper functioning of the transducer.

The miniature stepping-motor mounted on the biopsy device does radiate a stray magnetic field, but this field is very weak and will therefore not disturb the ultrasound transducer. However to ensure the total absence of a stray magnetic field, the stepping motor casing may be formed of a magnetic shielding metal such as steel.

A preferred stepping motor for use in the biopsy device control system is an HIS 20000 series 5 Vdc stepper motor produced by Hayden Switch and Instrument, Inc., Waterberry, Conn., U.S.A., or its model 26000 Series 5Vdc stepper motor. The same company also produces battery-powered dc pulse generators for driving these stepper motors, such as the SPECTRUM model 42103 Bipolar Driver. This driver which includes a variable frequency oscillator adapted to produce DC pulses at the desired repetition rate.

In the hybrid embodiment of the control system illustrated in FIG. 3, the stepping motor mechanism executes the first and second phases of an operating cycle, at the conclusion of which a tissue sample extracted from the internal target being biopsied is now loaded in the hollow needle.

The third and final phase is carried out by a pneumatic mechanism similar to that included in the first embodiment in which a suction pump in the unit 11 is external to the biopsy device and is coupled by flexible tube 30 to the syringe. The suction pump acts to draw air to create a negative pressure in the upper region SR in syringe 10 above the plunger 29 slideable within the cylindrical vessel 18 of the syringe.

This negative pressure in region SN cause plunger 19 to rise in cylinder 18 and in doing so to create a negative pressure or vacuum in region NR below the plunger this produces a suction force which draws the tissue sample out of the needle into region NR of the syringe. This sample is later removed form the syringe so that it can be analyzed.

Suction pump unit 11 is motor driven and may be self-sufficient and individually controlled so that when its motor is switched on by an operator, the pump then proceeds to manipulate the syringe until all of the tissue sample is transferred thereto at which point the pump is turned off.

A preferred arrangement for coordinating the operation of the stepping motor which carries out the first and second phases of the biopsy procedure and the pump motor which carries out the third phase is to provide an electronic control unit for the pump motor that it activated by a dc starting pulse PP yielded by controller 40 which supplies DC pulses to the stepping motor. The starting pulse PP generated at the conclusion of the second phase of the operating cycle is applied to a timer T in the electronic control unit for the pump motor. The timer acts to turn on the pump motor and to keep it in operation for a predetermined time period sufficient to permit full transfer of the tissue sample to the syringe, after which the pump motor is automatically switched off.

In practice, the hybrid control system shown in FIG. 3 for the FNA biopsy device may be fully automated by means of a computer adapted to govern the operation of both the pneumatically-operated and stepper-motor driven mechanisms. The computer is programmed to carry out all three phases of the biopsy procedure, the parameters of which are tailored to the needs of the patient being biopsied.

In the hybrid system shown in FIG. 3, the biopsy needle which injects the patient passes through a central passage 24 in the ultrasound transducer 12 so that the operator can observe on the monitor screen 15 the internal target 17 being biopsied and the needle 21 engaging this target.

Third Embodiment

Figure 4:
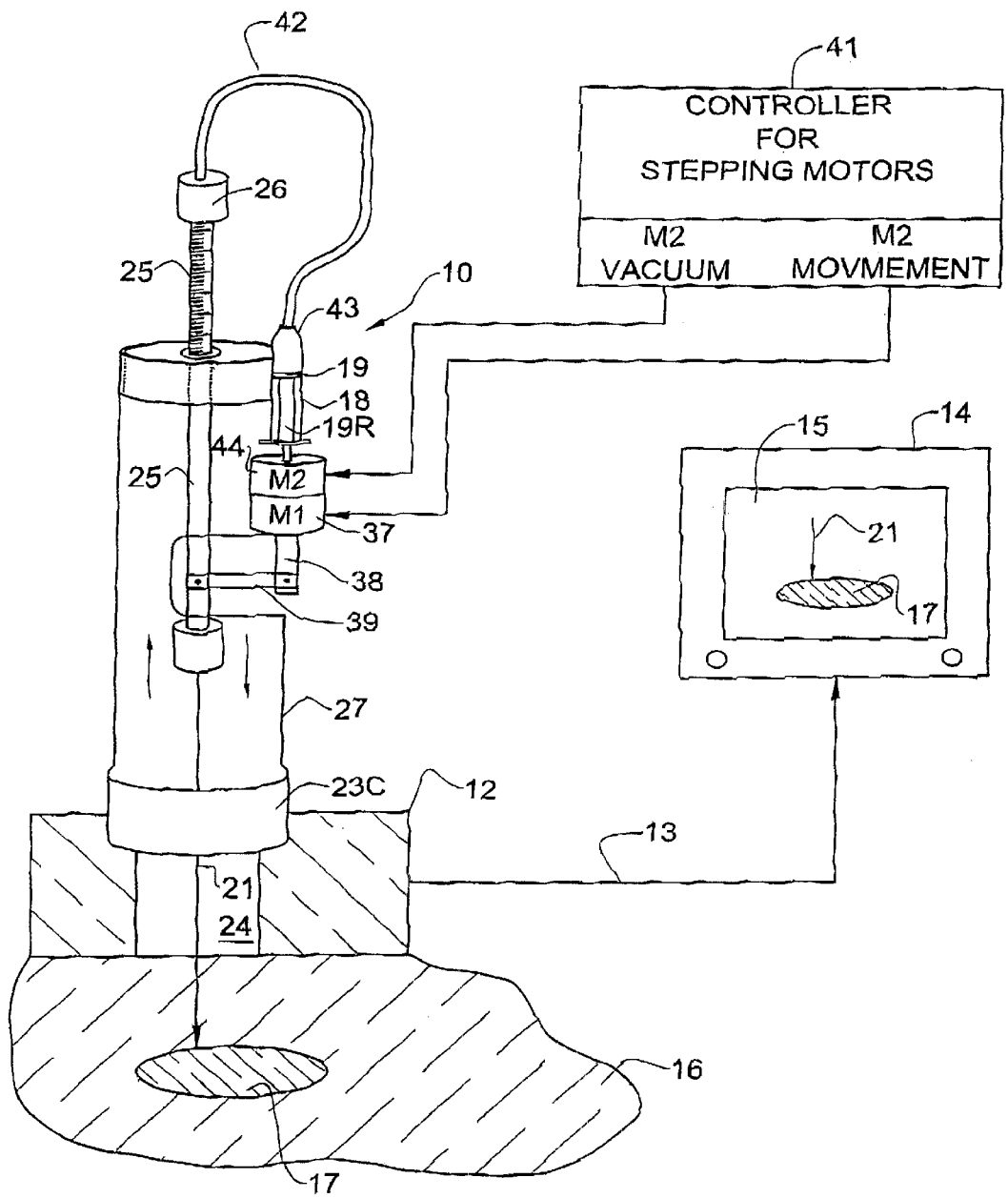
FIG. 4 schematically shows a third embodiment of the invention in which all three phases of an operating cycle of the biopsy device are motor controlled.

In this embodiment which is illustrated schematically in FIG. 4, all three phases of the biopsy procedure are carried out by stepping motors.

The first and second phases of the operating cycle are controlled as in the second embodiment by a stepping motor 37 energized by dc pulses produced in a controller unit 41, the ratchet bar 38 of this motor being operatively coupled by link 39 to the guide tube 25 carrying the biopsy needle 21. Stepping motor 37 is also identified as motor M1.

But in this embodiment, needle 21 does not project from the nose of syringe as in the embodiments illustrated in FIGS. 1 and 3, but is coupled to the syringe 10 by means of a flexible pipe 42 which extends from the nose 43 of the syringe to the upper end of guide tube 25 where it communicates with needle 21 therein.

The plunger 19 which is slideable within the cylinder 18 of the syringe is driven by a linear stepping motor 44 (also identified as motor M2) whose rack is joined to the axial drive rod 19R of plunger 19.

Motors M1 and M2 are energized by DC pulses generated in a controller 41 produced in the following sequence for carrying out the first, second and third phases of the operating cycle.

In practice, one can dispense with flexible pipe 42 and mount the nose 43 of the syringe directly into the upper end of guide tube 25, motor 42 then being above the syringe.

Phase I

In this phase, a train of dc pulses is produced by controller 41 which are applied to motor M1 in a polarity causing the needle to advance to engage the internal target and to extract a tissue sample therefrom.

Phase II

In this phase which follows phase I, a train of dc pulses is produced in a reverse polarity which is applied to motor M1, causing the needle to retract to withdraw the tissue sample from the patient.

Phase III

In the final phase which follows phase II, a train of dc pulses is produced which is applied to motor M2 in a polarity which causes plunger 19 to be pulled out to suck the tissue sample from the needle into the syringe.

Controller 41 may include a microprocessor that is programmable to tailor the operation of the system for controlling the biopsy device to the needs of particular patients.

While there has been disclosed and illustrated preferred embodiments of control systems for controlling the operation of an FNA biopsy device, it is to be understood that many changes may be made therein without departing from the spirit of the invention. Thus the generator for producing the dc pulses to energize the stepping motor for advancing the needle toward the target may have a variable pulse repetition rate. This makes it possible by increasing the pulse repetition rate to quickly advance the needle toward its target and when the needle approaches the target, it then slows down the pulse repetition rate so that the needle can be brought to an exact final position.

What is claimed is:

1. A system for controlling the operation of a fine needle aspiration biopsy device whose hollow needle is injectable into a patient's body to engage an internal target and extract therefrom a tissue sample which is then withdrawn from the target and transferred to a syringe communicating with the needle, said system comprising:

A. an axially shiftable guide tube surrounding the hollow needle which projects beyond the tube so that it can be injected;

B. means operatively coupled to the guide tube which in a first phase of a biopsy procedure axially advances the needle to inject it into the target to extract a tissue sample therefrom, and in a second phase axially retract the needle to withdraw the sample; and C. means operatively coupled to the syringe which in a third phase of the procedure manipulates the syringe to cause it to suck the tissue sample from the needle into the syringe.

2. A system as set forth in claim 1, in which the syringe includes a plunger slideable in a cylindrical vessel which when the plunger is pulled out produces a negative pressure creating a suction force, the means operatively coupled to the syringe acting to manipulate the plunger.

3. A system as set forth in claim 1, in which the means to advance and retract the needle includes a first linear stepping motor.

4. A system as set forth in claim 3, in which the stepping motor is energized by dc pulses which in said first phase has a polarity causing the needle to advance.

5. A system as set forth in claim 4, in which said dc pulses in said second phase are in a polarity causing the needle to retract.

6. A system as set forth in claim 3, in which said linear stepping motor is provided with a rack which with each de pulse applied to the motor moves one linear step, said rack being linked to the guide tube to translate its movement.

7. A system as set forth in claim 3, in which each step is a small fraction of an inch, whereby the needle can be precisely positioned.

8. A system as set forth in claim 3, in which the dc pulses are produced in a battery-powered pulse generator.

9. A system as set forth in claim 8, in which the pulse generator is adjustable to vary the repetition rate and the magnitude of the pulses.

10. A system as set forth in claim 3, in which the means to manipulate the syringe includes a second dc stepping motor.

11. A system as set forth in claim 10, in which the syringe includes a plunger which is axially movable in a cylindrical vessel and is coupled to said second stepping motor.

12. A system as set forth in claim 3, in which dc pulses for energizing the first stepping motor and for energizing the second stepping motor are derived from a common pulse generator.

13. A system as set forth in claim 1, in which the means to manipulate the syringe is pneumatically driven.

14. A system as set forth in claim 13, in which the pneumatic means includes a suction pump adapted to draw air out of the syringe to produce a negative pressure sucking the tissue from the needle into the syringe.

15. A system as set forth in claim 1, associated with an ultrasound imaging instrument having a transducer which when placed against the body of a patent then causes a monitor screen to display the tumor, said transducer having a guide passage thereon to receive the needle of the biopsy device whose advance toward the target is displayed on the screen.

16. A system as set forth in claim 15, in which the passage is of the dead center of the transducer to cause the needle to be properly displayed on the screen in its relationship with the target.

* * * * *